United States Patent [19]

Curry

[11] Patent Number: 5,037,400
[45] Date of Patent: Aug. 6, 1991

[54] APPARATUS FOR RESHEATHING HYPODERMIC NEEDLES

[75] Inventor: Robert L. Curry, Orange Park, Fla.

[73] Assignee: Oakleaf Enterprises, Inc., Jacksonville, Fla.

[21] Appl. No.: 175,419

[22] Filed: Mar. 30, 1988

[51] Int. Cl.[5] ............... A61M 5/32; B65D 83/10
[52] U.S. Cl. ..................... 604/192; 206/365
[58] Field of Search ........... 604/192, 197, 263, 283; 206/365, 366; 248/538

[56] References Cited

U.S. PATENT DOCUMENTS

| | | | |
|---|---|---|---|
| 2,417,626 | 3/1947 | Blocher | 206/365 |
| 2,659,485 | 11/1953 | Duley et al. | 206/365 |
| 3,307,552 | 3/1967 | Strawn | 604/283 |
| 3,658,061 | 4/1972 | Hall | 604/263 |
| 4,485,918 | 12/1984 | Mayer | 206/380 |
| 4,559,042 | 12/1985 | Votel | 604/263 |
| 4,573,975 | 3/1986 | Frist et al. | 604/263 |
| 4,596,562 | 6/1986 | Vernon | 604/192 |
| 4,610,667 | 9/1986 | Pedicano et al. | 604/263 |
| 4,623,336 | 11/1986 | Pedicano et al. | 604/263 |
| 4,629,453 | 12/1986 | Cooper | 604/192 |
| 4,654,034 | 3/1987 | Masters et al. | 604/263 |
| 4,659,330 | 4/1987 | Nelson et al. | 604/263 |
| 4,664,259 | 5/1987 | Landis | 604/192 |
| 4,717,386 | 1/1988 | Simmons | 604/263 |
| 4,737,149 | 4/1988 | Gillilan | 604/263 |
| 4,742,910 | 5/1988 | Staebler | 604/263 |
| 4,747,836 | 5/1988 | Luther | 604/263 |
| 4,781,697 | 11/1988 | Slaughter | 604/192 |
| 4,795,443 | 1/1989 | Permenter et al. | 604/263 |
| 4,799,927 | 1/1989 | Davis et al. | 604/192 |
| 4,802,579 | 2/1989 | Hall et al. | 206/366 |

FOREIGN PATENT DOCUMENTS

| | | | |
|---|---|---|---|
| 3433359 | 4/1986 | Fed. Rep. of Germany | 604/192 |
| 2586566 | 3/1987 | France | 604/192 |
| 2019219 | 10/1979 | United Kingdom | 604/283 |
| 2198644 | 6/1988 | United Kingdom | 604/192 |
| 8806462 | 9/1988 | World Int. Prop. O. | 604/263 |

Primary Examiner—C. Fred Rosenbaum
Assistant Examiner—Sharon Rose
Attorney, Agent, or Firm—Steven R. Scott

[57] ABSTRACT

An apparatus for resheathing hypodermic needles having a hollow cylindrical sheathguard to encompass a needle sheath inserted therein; a means of retaining the needle sheath within the sheathguard; a horizontal protective barrier below the aperture of the sheathguard and parallel thereto; a means for supporting the barrel of a hypodermic syringe engaged in the device; a means of guiding the syringe with hypodermic needle during resheathing; and a vertical protective barrier adjacent to the aperture of said sheathguard and perpendicular thereto.

4 Claims, 4 Drawing Sheets

APPARATUS FOR RESHEATHING HYPODERMIC NEEDLES

SUMMARY OF THE INVENTION

1. Nature of Invention

This invention relates generally to devices to guard against and/or prevent needle-stick injuries to individuals providing health care services in the handling and resheathing of hypodermic needles. In its simplest embodiment, it is provided with a hollow cylindrical sheathguard to encompass the needle sheath, and a means of engaging and retaining a hypodermic needle sheath inserted in the device. In further embodiments the device incorporates: A horizontal protective barrier below the aperture of the sheathguard and parallel thereto; a means of supporting the barrel of a hypodermic syringe engaged in the device; a means of guiding the syringe with hypodermic needle during resheathing; and a vertical protective barrier adjacent to the aperture of said sheathguard and perpendicular thereto.

2. Background of the Invention

Hypodermic needles pose serious threats to health care professionals who may contract, or come under the threat of contracting, serious diseases such as AIDS and hepatitis due to contact or skin penetration by contaminated needles. Attempts have been made to deal with this problem in a general manner in the patents described below. However, none of these patents are adapted to the particular needs of professionals exposed to the risk of injury and infection from hypodermic needles utilized in the practice of dentistry. This has led to a proliferation of devices advertised and offered for sale to dental professionals intended to meet the particular needs of health care workers in this area. Many of these devices have merit; however, none meet the dual needs of the dentist for both safety and convenience of usage. In its preferred embodiment, the instant invention meets these needs in a satisfactory and highly innovative manner, and is readily adapted for use by other health care professionals as well.

Prior patents reviewed consist of the following:

| Pat. No. | Date | Inventor |
| --- | --- | --- |
| 4,623,336 | November 18, 1986 | Pedicano etal. |
| 4,629,453 | December 16, 1986 | Cooper |
| 4,654,034 | March 31, 1987 | Masters etal. |
| 4,659,330 | April 21, 1987 | Nelson etal. |

In general, these patents consist of hypodermic needle sheaths with specialized features that assist in resheathing and sanitary disposal of the needle after a single use. The Pedicano patent teaches a disposable needle sheath with a funnel-shaped aperture for receiving and guiding a used needle into the sheath for disposal after use. The design is provided with a cap whereby the sheath containing the hypodermic needle can be sealed prior to disposal to prevent the spread of bacteria or other agents of infection. The Cooper patent describes another form of disposable sheath including a separate cap and a radially extending flange that acts, like the funnel-shaped aperture on the Pedicano patent, as a protective barrier for the fingers when the needle is returned to its protective sheath for disposal. The Masters patent discloses a form of needle sheath very similar to those claimed in Pedicano and Cooper, but with the addition of axial splines positioned to space the user's fingers away from the aperture of the sheath as an additional means of protecting against accidental needle sticks during resheathing. Finally, the Nelson patent describes a needle sheath having an elongated handle so that the user may resheath the needle without directly grasping the needle sheath and so avoid needle stick injuries.

None of these patents meet the distinctive requirements of those involved in the practice of dentistry. This failure arises in large part from the dental professions ability and need to use both dental syringe and hypodermic needle for the administering of multiple injections. The dental syringe, unlike the disposable syringe generally utilized for medical injections, is a permanent fully reusable dental instrument. The hypodermic needles used in conjunction with the dental syringe are generally utilized, during the course of a patient treatment session, to administer multiple anesthetic injections. The number may vary greatly depending on the nature and extent of treatment rendered, the passage of time during the treatment session, and the sensitivity of the individual treated. Thus, as an unsheathed hypodermic needle may become contaminated and pose a danger of injury and infection to those providing care, it is generally necessary to sheath and unsheath the needle several times during each treatment session.

The needle sheaths described in the aforesaid patents are designed and adapted for a single use followed by immediate disposal. In fact, some are provided with automatic locking means which prevent subsequent removal after they are resheathed. Further, these designs are not generally available or in use for the sheaths provided with dental hypodermic needles. Finally, due to the small size of the protective shields and the use of light weight plastics in manufacture, their value is extremely limited. The problems caused by the small size of the protective shield should be immediately obvious. The dangers arising from the nature of the material utilized is well known to the inventor from personal experience in the field. He is aware of numerous incidents where hypodermic needles have penetrated the side of the sheath during resheathing and caused needle-stick injuries. This danger is exacerbated and made more difficult to avoid by the greater than normal length of some needles utilized in the administration of anesthetic during a dental treatment session.

The great need for suitable protective means has led to the proliferation of devices aimed at helping dental professionals avoid needle-stick injuries. The inventor is personally familiar with four types of devices in current use. First, a freestanding device comprised of an integrally formed plastic cylinder joined at one end to a base incorporating a suction cup. Second, a more dimensional freestanding device having a centrally located vertical cylindrical bore. Third, a simple puncture resistant card that can be used either in a freestanding or a hand-held manner. Fourth, a funnel-shaped hand-held device integrally formed of autoclavable high density plastic.

Examples of the first and second types of devices are found, respectively, in the "Needle Resheather" manufactured by Concord Laboratories, Inc., and the "Cap Caddy" manufactured by Concord Laboratories, Inc. Both devices are basically stands that engage the protective sheath of the syringe needle.

In utilizing these devices, the syringe and hypodermic needle are separated from the sheath which remains engaged in the device in a vertical position with its open aperture elevated. After administering an injection, resheathing is accomplished by guiding the point of the hypodermic needle downward into the open aperture of the protective sheath.

An example of the third type of device is found in the "Needle Shield" manufactured by Cottrell, Ltd. The "Needle Shield" is merely a puncture resistant card with a hole through which the protective sheath of the hypodermic needle can be inserted and remain at a 90° angle to the surface of the card. In a hand-held resheathing operation the card acts as a barrier against needle-stick injuries if the tip of the hypodermic needle misses the open aperture of the needle sheath. It can also serve as a prop for the needle sheath, holding it with its aperture elevated to form a more accessible target for the hypodermic needle. This allows the dental professional to avoid holding the needle sheath as the hypodermic needle is inserted.

An example of the fourth type of device is found in "Aim Safe" manufactured by Cottrell, Ltd. "Aim Safe" is used by inserting the needle sheath into the hollow central bore of the device with the wide end directed toward the syringe. The material utilized is flexible enough to allow the cylindrical portion encompassing the needle sheath to be compressed by the fingers, thereby allowing the user to grip the sheath through the device for the withdrawal of the hypodermic needle from the sheath. The device can then be left loosely on the needle sheath until resheathing. During resheathing the wide funnel-shaped guard and cylindrical barrel are reputed to protect the fingers against accidental needle-stick by a poorly directed needle.

It will be noted that all of the devices that have been developed and put into use by the dental community share a common feature that distinguishes them from the previously cited patents: They are designed not to function as needle sheaths, but to encompass the needle sheath and facilitate the safe, effective handling and utilization of the hypodermic needles and sheath through multiple resheathings. However, all have defects that seriously limit their utility as dental implements and/or protective devices. The freestanding devices suffer primarily from a lack of utility as dental implements, while the hand-held devices are seriously limited in their protective value. In addition, both types of devices are limited in their value in supporting and retaining a syringe between injections. Finally, none of these devices is provided with any means of directing and guiding the movement of the syringe into proper alignment for insertion into the device. These facts will become clear upon a review of the manner in which these devices are used in the context of dental surgery.

Dental surgery is commonly and most efficiently performed with a dental assistant. The dentist and the assistant face each other across the patient with the assistant handing the dental surgeon, upon request, the implements necessary to the procedure performed. These transfers, including the transfer of dental syringes, take place below the patient's chin and outside of the patient's line of sight. This mode of operation is not possible with the freestanding devices reviewed. To effect resheathing without assistance, the dentist will be required to turn and/or move from the operative area to the area where the freestanding device is located. In the alternative, the syringe with hypodermic needle would need to be handed to the assistant for resheathing, creating additional dangers of needle stick injury due to the transfer. Thus, these devices are seriously limited in their utility as dental implements.

The hand-held devices currently in use, while more adapted to dental procedures, lack features important to promote safe handling and transfer of the syringe. The third type of device, as exemplified in the "Needle Shield" manufactured by Cottrell, Ltd., provides no protection for the hand holding the needle sheath from injury if the sheath is penetrated by the needle during resheathing. This problem is also inherent in the design of the fourth type of device, as exemplified in "Aim Safe" produced by the same manufacturer. This device, while providing a cylindrical shield encompassing the sheath, is required to be produced from flexible materials in a manner that allows easy compression of same. This feature is necessary so that the sheath may be grasped and held for unsheathing and resheathing of the hypodermic needle. Unfortunately, it also appears to dictate the use of materials of a type and thickness that are inherently susceptible to penetration by the longer than normal needles used in dental practice. Further, both fail to provide protection for the hand of the dental assistant which accepts and/or provides support to the barrel of the syringe. In most transfers, the assistant is required to use one hand to hold the sheath while simultaneously accepting and/or providing support for the barrel of the syringe with the other. The hand providing support for the barrel of the syringe is susceptible to injury by the tip of the needle as it is withdrawn from the sheath. The hand is also unprotected by the current devices while moving to support the barrel of the syringe and/or assist in the resheathing process.

Prior freestanding and hand-held devices are also limited in their usefulness and/or safety as a support for the syringe and hypodermic between injections. The freestanding devices might possibly be used to support the device in a vertical position via the needle sheath engaged on the hub of the syringe, holding the assembly in a vertical position with the thumb ring of the syringe elevated. However, a hypodermic in this position is highly susceptible to being dislodged from its position and connection with the needle sheath if accidently struck or jarred. It can then be subject to damage or cause needle-stick injury to dental surgeon, assistant or patient. The hand-held devices make no attempt to provide support for the syringe when it is set aside between injections. If left in position on the sheath after the syringe is set aside, they typically result in the syringe being supported in a generally horizontal position via the device's connection with sheath and needle hub, and the thumb ring of the syringe. This position stresses portions of the syringe not designed to serve as supports for its weight. Thus, neither the freestanding nor the hand held devices can realistically be used to support the syringe between injections. Instead, they must be removed with resultant delays in dental procedures.

Finally, none of these devices is provided with any means of guiding and directing the movement of the hypodermic needle into a sheath engaged in the device. The primary cause of needle-stick injury is a failure to properly align the hypodermic needle with the aperture of the sheath while seeking to insert the needle into the same. Thus, this is obviously a serious design limitation.

3. Objects of the Invention

It is the object of this invention to provide a device that is adapted to help protect against needle-stick injury during the process of resheathing a hypodermic needle.

It is a further object of this invention to provide a device that is compact, light in weight, and otherwise adapted to be hand-held during the resheathing process.

It is also an object of the current invention to provide in such a device an inpenetrable protective flange or barrier that protects the hand holding the device from injury if the aperture of the sheath is missed while attempting to resheath the hypodermic needle as well as an inpenetrable cylindrical barrier that surrounds and encompasses the sheath to protect the hand holding the device from injury if a hypodermic needle penetrates the sheath during resheathing.

A further object of this invention is to provide a means for guiding and retaining the sheath within the device as the hypodermic needle is withdrawn that also allows the device to be manufactured from rigid, inpenetrable materials. This is accomplished in the first instance by the utilization of a simple pressure operated lever that engages the needle sheath when compressed. In an alternative embodiment, this is accomplished by incorporating tapering screw threading within the bore of the device.

Another object of this invention is to protect the hand of the dental assistant that provides support for the barrel of the syringe during both unsheathing and resheathing of the hypodermic needle. Thus, alternate embodiments of the present invention incorporate a horizontal protective barrier that is generally parallel to the axis of the syringe while engaged by the device.

A further object of this invention is to provide stable balanced support for the syringe while it is engaged in the device. This is accomplished by utilizing the horizontal protective barrier or a clamp having its base thereon, as a means of support for the barrel of the syringe.

Another object of this invention is to provide a means of assisting in guiding the hypodermic needle into the open aperture of the sheath. Thus, one embodiment of the present invention incorporates a groove in the supporting surface provided by the horizontal barrier that acts to guide and direct the syringe during resheathing. In alternative embodiments this is accomplished by utilizing a clamping means that aligns the axis of the syringe and hypodermic needle with the axis of the sheath during the resheathing process.

A still further object of this invention is to minimize the dangers of puncture injury that arise because the syringe and needle are initially engaged in the device by thrusting same along the axis of the syringe and needle. In the last two embodiments shown, the needle is not initially moved toward the sheath along the line of their common axis. This movement maximizes the possibility of an accidental puncture wound. The embodiments referenced allow the syringe to be initially engaged in the device by a movement that is generally perpendicular to the axis of the needle. They then allow the syringe to be safely locked into a position aligned with the axis of the sheath prior to being thrust into an engaged position in the sheath.

A further purpose is to provide a means of support for the barrel of the syringe that is removable after use for disposal or sterilization. This allows the device to be utilized through multiple patient treatment sessions without being sterilized as neither the barrel of the syringe nor the needle thereof contacts the body of the device.

It is also an object of this invention to provide a device that is designed for use with, and adaptable to, many different sizes and types of hypodermic needle sheaths, that is inexpensive to produce, and convenient to use.

The above and other features of the invention will be more fully understood from the detailed description and the accompanying drawings.

DETAILED DESCRIPTION OF THE INVENTION

Figure 1:
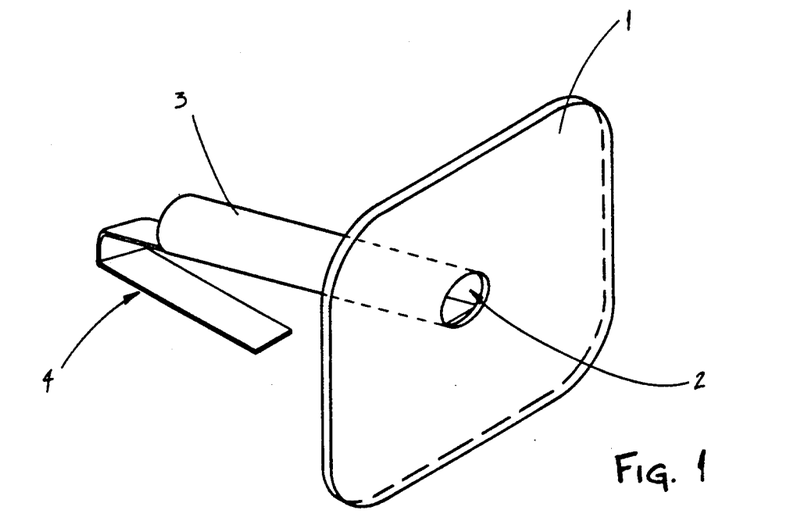
FIG. 1 is a perspective view of the simplest embodiment of the present invention revealing a cylindrical sheath guard with a hollow central bore, protective shield, and a compression actuated means of engaging the needle sheath.
Figure 2:
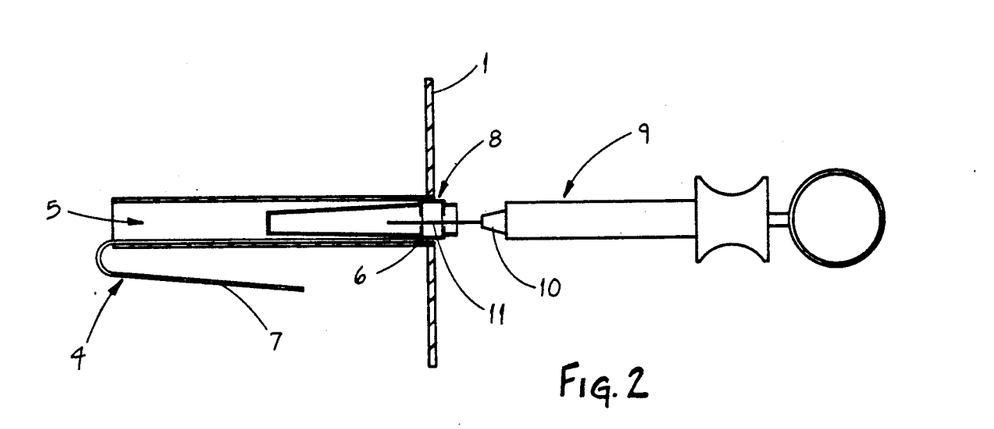
FIG. 2 is a longitudinal cross-sectional view of the simplest embodiment of this invention also revealing, for illustrative purposes, the means in which the hypodermic syringe and sheath are engaged by the device.

The first embodiment of the invention is illustrated in FIGS. 1 and 2. In this embodiment a protective shield 1 surrounds the receiving aperture 2 of a hollow cylindrical sheath guard 3 that incorporates a simple pressure actuated means 4 of engaging the sheath 8 of a hypodermic needle 11 shown partially inserted into the central bore 5 of the device. It should be recognized that the size and shape of the protective barrier may vary substantially without departing from the inventive concept. In particular, this barrier may take a variety of flat configurations, such as squares, hexagons or other polygons, as well as the simple rectangular shield shown. It may also be funnel-shaped, semi-spherical, or have some other three-dimensional configuration.

The device is most easily utilized by grasping the hollow cylindrical sheath 3 in one hand with the thumb and index finger adjacent to the protective shield 1 and the fingers of the hand positioned across and around the exterior portion 7 of the pressure actuated means 4 of engaging the needle sheath 8. In the embodiment shown in FIGS. 1 and 2, this pressure actuated means 4 is in the form of a "U" shaped lever arm that is attached at one of its ends to the lower interior surface of the hollow cylindrical sheath guard 3 by means of a hinge 6. When pressure is applied to the exterior portion 7 of the pressure actuated means 4 of engaging the needle sheath 8 by the fingers of the hand holding the device, the needle sheath 8 is pressed against the upper interior surface of the central bore 5, frictionally engaging the sheath 8 along both upper and lower surfaces and preventing it from being withdrawn from, or moved within the device. Thus, by the application of pressure to the exterior portion 7 of the engaging means 4, the sheath 8 may be firmly grasped within the device.

In its normal position on the syringe with hypodermic needle 9, the needle sheath 8 is held in place by frictional contact between the needle hub 10 and the interior surface of the sheath. This frictional contact is normally overcome, the sheath 8 separated from the hub 10, and the needle 11 withdrawn, by firmly grasping the sheath 8 and the hypodermic 9 and moving them in opposite directions along their common longitudinal axis. In resheathing, this movement is reversed. However, both actions require the sheath 8 to be held in position, and/or grasped with a degree of firmness sufficient to overcome the frictional resistance between the needle hub 10 and the interior surface of the sheath 8. As will be obvious to those familiar with the art, the previously described means of engaging the sheath within the device thereby allows both unsheathing and resheathing to be accomplished without direct contact between the hand and the hypodermic needle sheath 8. The inventive concept is not, however, limited to the engaging means 4 that is shown. In particular, it is possible to provide several alternate means of engaging and holding the sheath within the device that are actuated by applying pressure to trigger, button, lever, or other point exterior to the sheath guard 3; as well as to provide alternate means that are biased by spring or otherwise to automatically engage a sheath 8 inserted within the device; without superceding the inventive concept embodied herein.

Figure 3:
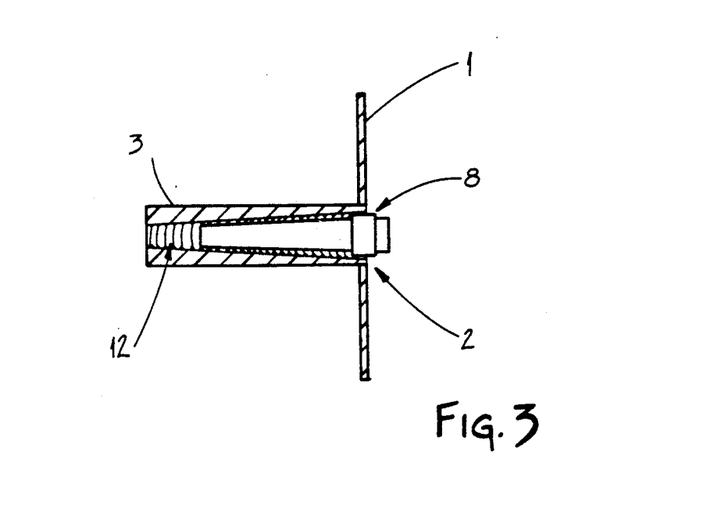
FIG. 3 is a longitudinal cross-sectional view of the second embodiment of this invention revealing a tapering, screw threaded central bore as an alternate means of engaging the syringe sheath shown inserted, for illustrative purposes only, in the device.

A second embodiment of this invention is set forth in FIG. 3. This embodiment differs from the embodiment diagrammed in FIGS. 1 and 2 in the means and method utilized to engage, hold, and disengage the sheath. The means utilized in the second embodiment is a screw threaded central bore 12 that tapers from its widest point at the aperture of the device 2 to its narrowest point at the opposite end of the sheath guard 3. To utilize this means, the sheath 8 is initially inserted into the device by direct translational movement along the longitudinal axis of the sheath 8 and the sheath guard 3. After the needle sheath 8 has been inserted into the device to the point where the width of the central bore 12 is equal to the width of the needle sheath 8, further engagement will require rotational as well as translational movement of the sheath in the manner commonly used with screw threaded devices. As will be recognized, the tapering interior allows the device to be utilized with sheaths of different widths without problem. Wider sheaths will merely contact and engage the screw thread at a point nearer to the aperture 2 of the device.

In practice it has been found that a half turn of the needle sheath 8 is generally sufficient to firmly engage same within the device. After the sheath 8 has been engaged by the screw threaded central bore of the device 12, it will retain its position through multiple insertions and withdrawals of the hypodermic needle 11. To disengage the sheath 8, the process is reversed. This means of engaging and holding the sheath within the device is also suitable for FIGS. 4, 5, 6, 7, 8 and 9. However, in order to avoid unnecessary and repetitive illustrations, the engaging means described with reference to FIGS. 1 and 2 is shown in all of these figures. It will, nonetheless, be understood that the means of engaging the sheath described with reference to FIG. 3 may be used with these embodiments as well.

Figure 4:
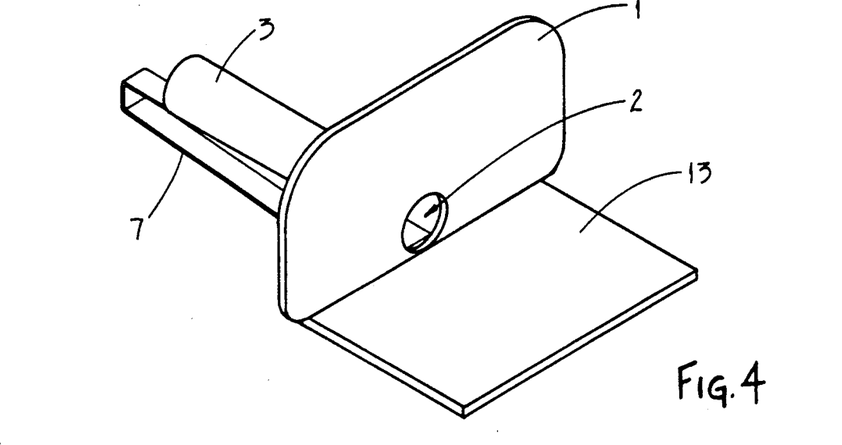
FIG. 4 is a perspective view of a third embodiment of the present invention having a horizontal extension which may serve both as a protective shield and a source of support for the barrel of a hypodermic syringe inserted therein.

FIG. 4 illustrates an embodiment of the device having a horizontal protective barrier 13 below the aperture 2 of the sheath guard 3 and parallel to its longitudinal axis. The horizontal protective barrier 13 illustrated in FIG. 4, as well as those illustrated in FIGS. 5, 6, 7, 8 and 9, serve as means of support for the syringe when the device is being held by the dental professional and when it has been set aside between injections. When set aside, the horizontal protective barrier 13 serves as a stable base for the device as a whole. In utilizing this embodiment of the device and those illustrated in FIGS. 5, 6, 7, 8 and 9, the dental assistant, whether accepting or conveying a syringe with the device, may accomplish the transfer with one hand due to the support given to the barrel of the syringe by the horizontal protective barrier 13. However, if the assistant uses both hands in utilizing this or any other of the embodiments featuring the horizontal protective barrier 13, the hand normally used to support the syringe will be below, and protected from accidental needle-stick injury by the horizontal protective barrier 13.

Figure 5:
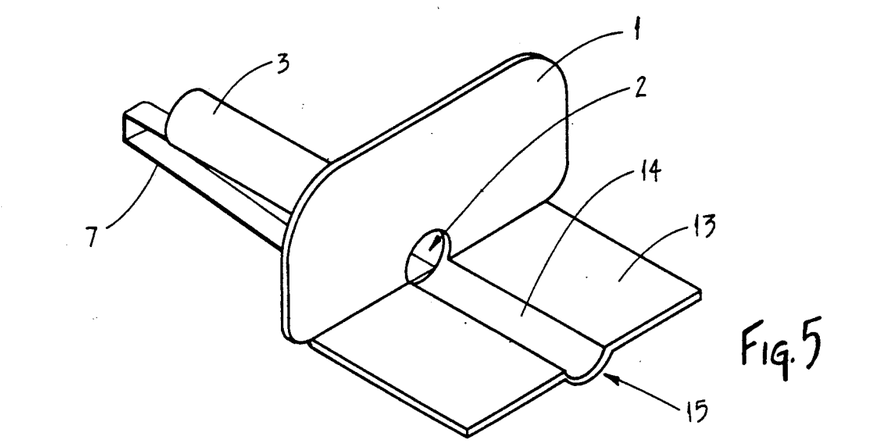
FIG. 5 is a perspective view of a fourth embodiment of the present invention wherein the horizontal extension incorporates a groove or trough that serves to guide the movement of the syringe while engaging with the device and to stabilize its position on the horizontal extension after the syringe has engaged the device.

A further refinement of this design is illustrated in FIG. 5, wherein the horizontal protective barrier 13 incorporates a groove 14 extending from the aperture 2 of the device and parallel to the longitudinal axis of the sheath guard 3. The groove 14 serves as a means of guiding the syringe while inserting sheath or needle into the device, and of stabilizing the syringe in proper position on the horizontal protective barrier 13 while it is engaged in the device. The groove 14 need not be formed by creating a depression in the horizontal protective barrier 13, as shown, but may be formed in a raised section of the horizontal protective barrier 13. Further, it may take a variety of configurations other than the semicylindrical shape shown. However, all designs are subject to the requirement that the longitudinal axis of a hypodermic syringe laid in the groove 14, or any variation thereof, be aligned with the longitudinal axis of the sheath guard 3.

In this embodiment, as well as those described in FIGS. 6, 7, 8 and 9, the design interposes or allows an intermediate step in the process of engaging the syringe in the device: Rather than moving the hypodermic needle of the syringe directly toward the sheath guard 3, the syringe is initially moved downward toward the groove 14 or other guiding means provided in the device. Only after the syringe is engaged therein and properly aligned with the sheath guard 3, is the syringe and hypodermic needle thrust into the sheath guard 3. Most needle-stick injuries sustained during resheathing occur due to a failure to properly align the longitudinal axis of hypodermic needle and sheath. It is believed that this feature in combination with the other unique advantages of the instant invention will substantially eliminate this type of injury.

Figure 6:
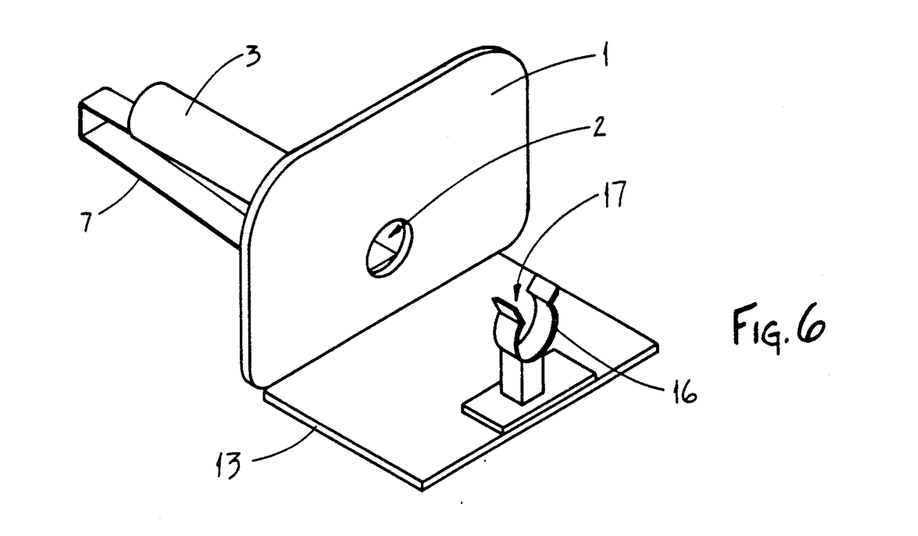
FIG. 6 is a perspective view of a fifth embodiment of the present invention wherein the syringe does not directly contact the horizontal extension, but is held by, and rests on an elevated clamping means aligned with the axis of the central bore of the device. Said clamping means serves as a means of guiding the movement of the syringe while engaging with the device, and stabilizes its position after the syringe is engaged in the device.

FIG. 6 illustrates a further variation of the embodiment described in FIG. 5, wherein the guiding means and proximate source of support for the syringe while engaged in the device are raised above the surface of the horizontal protective barrier 13. This guiding and supportive means 16 is aligned with the central axis of the sheath guard 3 and necessarily possesses a peripheral opening 17 or other means by which a syringe may be placed therein without requiring the syringe to be thrust along its longitudinal axis. The guiding and supporting means 16 of the type drawn is required to be produced of material with sufficient elasticity to allow the edges of its peripheral opening 17 to be forced apart by moderate pressure as a syringe is laid therein. The diameter of the guiding and supporting means 16 of the type shown is approximately equal to that of the standard syringes currently utilized, and thus firmly holds the syringe in place when placed therein. In practice, it has been found that a guiding and supporting means 16 of the type shown, that contacts the barrel of a syringe engaged therein for approximately one to two centimeters along its length, will hold said syringe in alignment with the central axis while allowing the syringe to be thrust along said axis toward the sheath guard 3. It has also been found that the optimal distance between the aperture 2 of the sheath guard 3 and the guiding and supporting means 16 is approximately 4 centimeters. At this distance, the guiding and supporting means 16 provides balanced support to the barrel of the hypodermic syringe and does not contact the hypodermic needle of the syringe as it is being freed from, or engaged in, sheath guard 3.

Figure 7:
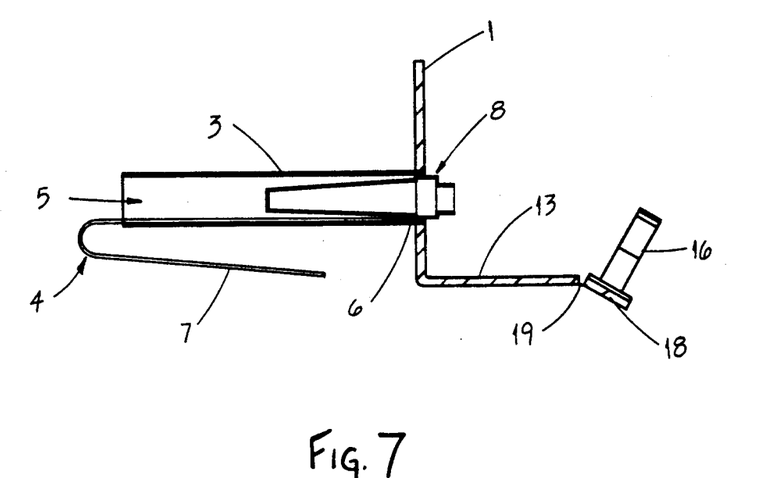
FIG. 7 is a longitudinal cross-sectional view of a sixth embodiment of the present invention wherein that portion of the horizontal extension bearing the clamping means is hingeably connected to the remainder of the horizontal extension, allowing the hinged portion to pivot below the horizontal in the manner shown.
Figure 8:
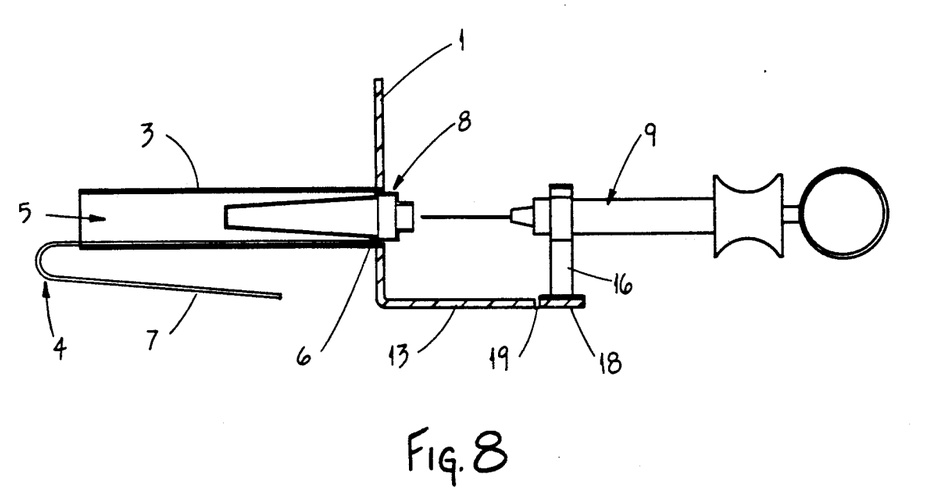
FIG. 8 is a longitudinal cross-sectional view of the sixth embodiment of the invention wherein the clamp bearing section of the horizontal extension has been pivoted upward, supporting the hypodermic syringe slidably engaged therein, which is shown for illustrative purposes only, and aligning same with the axis of the central bore of the device.

FIGS. 7 and 8 illustrate a further refinement of the invention wherein the horizontal extension 13 bears a pivoting section 18 which may be inclined below the horizontal extention 13 by approximately 45° as shown in FIG 7. FIG. 8 shows the pivoting section 18 after being brought into alignment with the remainder of the horizontal extension 13. In these figures the pivoting section 18 is connected to the remainder of the horizontal extension 13 by a connector 19. The connector 19 in the device as illustrated is merely a portion of the horizontal extension 13 that has been thinned or grooved to the degree necessary to render it flexible. In the alternative, the connector 19 may be formed of a flexible material or a standard hinge attached to both the pivoting section 18 and the remainder of the horizontal extension 13.

It has been found that the initial step taken to engage the syringe in the embodiments shown in FIGS. 5, 6, 7, 8 and 9 is generally and most simply to contact the guiding and supporting means with the hypodermic needle and barrel of the syringe inclined approximately 45° above the horizontal. Thus, in utilizing the embodiment shown in FIG. 5, the midpoint of the syringe barrel is first brought into contact with the edge 15 of the groove 14 with the hypodermic needle and syringe barrel elevated. The needle bearing end of the syringe is then lowered into the groove 14 while maintaining contact between the midpoint of the syringe's barrel and the outermost edge 15 of the groove 14. A similar means of approach is generally utilized with the embodiments shown in FIGS. 6, 7, 8 and 9. The pivoting section 18 allows the peripheral opening 17 of the guiding and supporting means 16 to be inclined at the same angle as the syringe which is being engaged therein. This allows the guiding and supporting means 16 to more easily accept and engage the barrel of the syringe.

Figure 9:
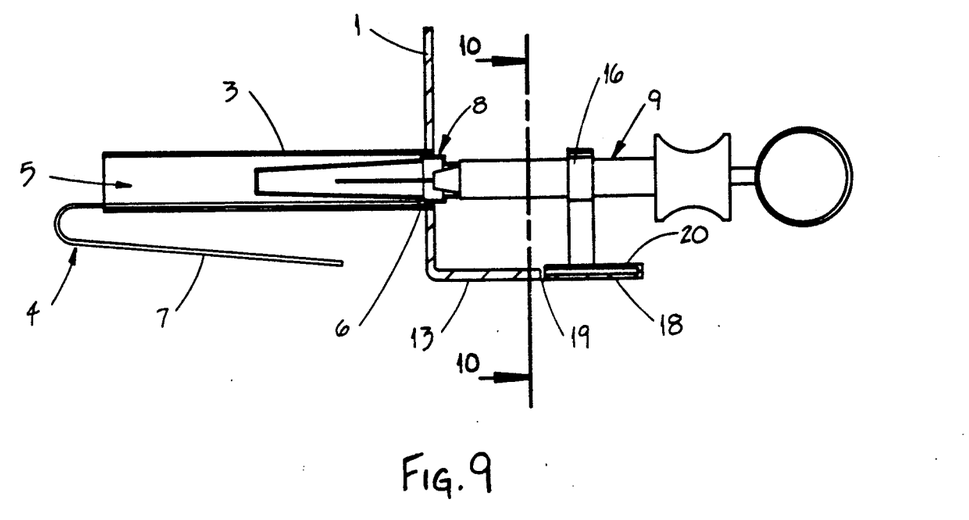
FIG. 9 is a longitudinal cross-sectional view of a seventh embodiment of the present invention wherein the clamping means is engaged in, and connected to, the pivoting section of the horizontal extension by sliding the clamping means into a slot in said pivoting section having a width slightly larger than the clamping means shown.

FIG. 9 illustrates the preferred embodiment of the instant invention wherein the guiding and supporting means 16 is engaged and held in a slot 21 formed in the pivoting section 18 of the horizontal extension 13. The barrel of the syringe as well as the hypodermic needle may also be contaminated by patient contact. Thus, the feature described allows the only portion of the device which comes into direct contact with, and may be contaminated by, the syringe to be easily replaced. The device taught herein may, therefore, be utilized for numerous patients without the necessity of sterilizing the device as a whole by merely replacing the guiding and supporting means 16 between each patient.

Figure 10:
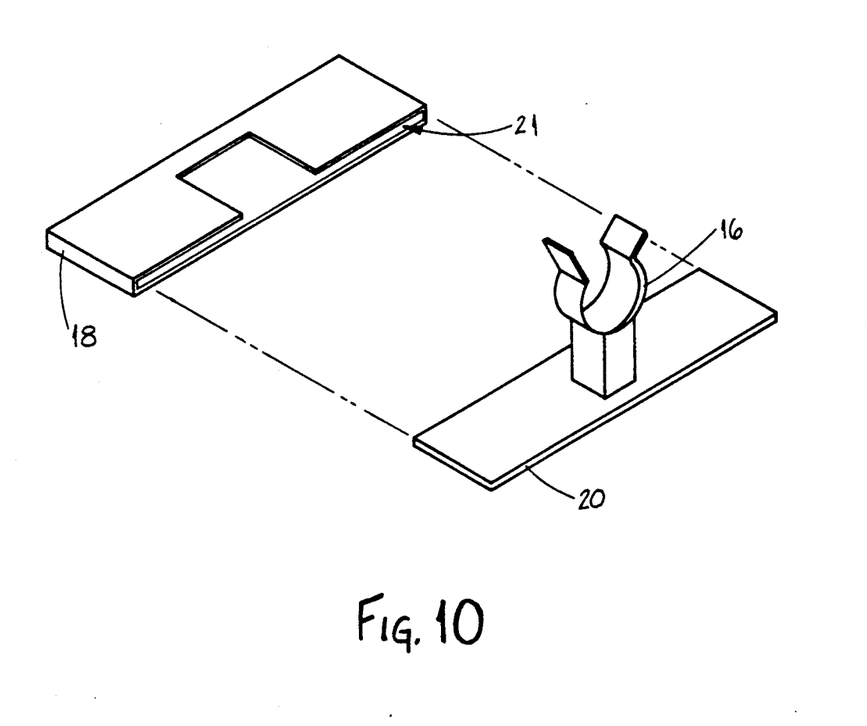
FIG. 10 is a perspective view of the pivoting section of the horizontal extension and of the clamping means, illustrating the nature of the slot in the pivoting section of the horizontal extention and the complementary shape of the base of the clamping means.

FIG. 10 illustrates the nature and shape of the slot 21 provided in the pivoting section 18, and the manner in which it is shaped and formed to snugly hold and engage the base of the guiding and supporting means 16. In the device as shown, the slot 21 is positioned on the side of the pivoting section 18 closest to the protective shield 1. Thus, the guiding and supporting means 16 may only be engaged in or removed from the device when the pivoting section 18 is inclined below the vertical. However, as should be obvious, numerous alternate means of attaching the guiding and supporting means 16 to the pivoting section 18 could be utilized.

It should also be noted that further amalgams of, and additions to, the embodiments shown are possible within the inventive concept Thus, it is possible to combine the embodiments shown in FIGS. 7, 8, 9, and 10. In this amalgam, the horizontal protective barrier 13 of the type shown in FIG. 5 is provided at its edge farthest from the aperture of the sheath guard 3, with a member extending downward. A pivoting section 18 provided with a guiding and supporting means 16 of the type shown in FIGS. 7, 8, 9, and 10 is hingeably attached to the member extending downward from the horizontal protective barrier 13 such that the longitudinal axis of a syringe and hypodermic needle engaged therein will, once the pivoting section is swung into position parallel to the horizontal protective barrier 13, be aligned with the longitudinal axis of the needle sheath guard. It is also possible to provide a sterile disposable covering for the proximate means of support for the hypodermic syringe engaged in the device while remaining within the spirit of this invention.

This invention is not, however, to be limited by the embodiments shown in the drawings and described herein, which are only given by way of example and illustration and not of limitation. It will be recognized that here, as in all other areas, numerous variations and modifications may be resorted to without departing from the spirit of the invention.

What is claimed is:

1. An apparatus for resheathing hypodermic needles comprising:
   - a needle sheath guard having a hollow cylindrical bore for containing and encompassing a hypodermic needle sheath inserted therein;
   - a means whereby a hypodermic needle sheath inserted within the needle sheath guard may be removably retained therein; and
   - a horizontal protective barrier positioned below the aperture of the needle sheath guard and parallel to the longitudinal axis thereof with a trough in its surface serving as a means of aligning the longitudinal axis of a hypodermic syringe engaged therein with the longitudinal axis of the needle sheath guard prior to its insertion therein.

2. An apparatus for resheathing hypodermic needles, comprising:
   - a needle sheath guard having a hollow cylindrical bore for containing and encompassing a hypodermic needle sheath inserted therein;
   - a means whereby a hypodermic needle sheath inserted within the needle sheath guard may be removably retained therein; and
   - a means for supporting the barrel of a syringe engaged in the device in a generally horizontal position aligned with the longitudinal axis of the needle sheath guard wherein the portion of the means of support for the barrel of a hypodermic syringe engaged in the device which physically contacts the said barrel can be removed and replaced.

3. An apparatus for resheathing hypodermic needles, comprising:
   - a needle sheath guard having a hollow cylindrical bore for containing and encompassing a hypodermic needle sheath inserted therein;
   - a means whereby a hypodermic needle sheath inserted within the needle sheath guard may be removably retained therein; and
   - a means for supporting the barrel of a syringe engaged in the device in a generally horizontal position aligned with the longitudinal axis of the needle sheath guard wherein the means for supporting the barrel of a hypodermic syringe in a generally horizontal position while engaged therein is connected to, and supported by, a horizontal barrier positioned below the aperture of the needle sheath guard and parallel to the longitudinal axis thereof, and that portion of the horizontal protective barrier which is connected to, and supports, the means for supporting the barrel of a hypodermic syringe is pivotally connected to the remainder of the horizontal protective barrier such that said portion may be inclined below the plane of said horizontal protective barrier.

4. An apparatus for resheathing hypodermic needles, comprising:
   - a needle sheath guard having a hollow cylindrical bore for containing and encompassing a hypodermic needle sheath inserted therein;
   - a means whereby a hypodermic needle sheath inserted within the needle sheath guard may be removably retained therein; and
   - a means for aligning the longitudinal axis of a hypodermic syringe engaged therein with the longitudinal axis of the needle sheath guard prior to insertion therein, said means being connected to, and supported by, a horizontal protective barrier below the aperture of the needle sheath guard and parallel to the longitudinal axis thereof and that portion of the horizontal protective barrier that is connected to, and supports, the means for aligning the longitudinal axis of a hypodermic syringe engaged with the longitudinal axis of the needle sheath guard is pivotally connected to the remainder of the horizontal protective barrier such that said portion may be inclined below the plane of said horizontal protective barrier.

* * * * *